United States Patent
Bek et al.

(10) Patent No.: US 8,449,529 B2
(45) Date of Patent: *May 28, 2013

(54) SYSTEMS AND METHODS FOR MONITORING AND CONTROLLING USE OF MEDICAL DEVICES

(75) Inventors: Robin Bek, Campbell, CA (US); John Gaiser, Mountain View, CA (US); Jay Qin, Fremont, CA (US); David S Utley, Redwood City, CA (US)

(73) Assignee: Mederi Therapeutics, Inc., Greenwich, CT (US)

( * ) Notice: Subject to any disclaimer, the term of this patent is extended or adjusted under 35 U.S.C. 154(b) by 1205 days.

This patent is subject to a terminal disclaimer.

(21) Appl. No.: 12/315,890

(22) Filed: Dec. 8, 2008

(65) Prior Publication Data

US 2009/0093805 A1 Apr. 9, 2009

Related U.S. Application Data

(60) Division of application No. 10/974,454, filed on Oct. 27, 2004, now Pat. No. 7,465,301, which is a division of application No. 09/974,750, filed on Oct. 10, 2001, now Pat. No. 6,827,713, which is a continuation of application No. 09/495,390, filed on Jan. 30, 2000, now abandoned.

(51) Int. Cl.
*A61B 18/14* (2006.01)

(52) U.S. Cl.
USPC .................................. 606/1; 606/34; 606/41

(58) Field of Classification Search
USPC .................................. 606/1, 32–34, 41, 45–50
See application file for complete search history.

(56) References Cited

U.S. PATENT DOCUMENTS

| | | | |
|---|---|---|---|
| 4,858,615 A | 8/1989 | Meinema | |
| 5,363,347 A | 11/1994 | Nguyen | |
| 5,383,874 A * | 1/1995 | Jackson et al. | 606/1 |
| 5,651,780 A | 7/1997 | Jackson et al. | |
| 5,742,718 A * | 4/1998 | Harman et al. | 385/53 |
| 5,743,903 A | 4/1998 | Stern et al. | |
| 5,848,969 A | 12/1998 | Panescu et al. | |
| 6,106,460 A | 8/2000 | Panescu et al. | |
| 6,165,169 A | 12/2000 | Panescu et al. | |
| 6,387,092 B1 * | 5/2002 | Burnside et al. | 606/32 |
| 6,391,024 B1 | 5/2002 | Sun et al. | |
| 6,464,689 B1 | 10/2002 | Qin et al. | |
| 2002/0193787 A1 | 12/2002 | Qin et al. | |
| 2002/0198519 A1 | 12/2002 | Qin et al. | |

FOREIGN PATENT DOCUMENTS

| | | |
|---|---|---|
| EP | 0765813 | 4/1997 |
| WO | WO99/17671 | 4/1999 |

\* cited by examiner

*Primary Examiner* — Michael Peffley

(57) ABSTRACT

A usage key card is adapted to be handled separate from a device tissue treatment device. The usage key card has a storage medium formatted to contain an identification code, which is unique to the usage key card. The usage key card is also adapted to be read by a reader separate from the device. The storage medium is also formatted, when inserted into the reader, to retain data generated pertaining to operation of the device.

18 Claims, 8 Drawing Sheets

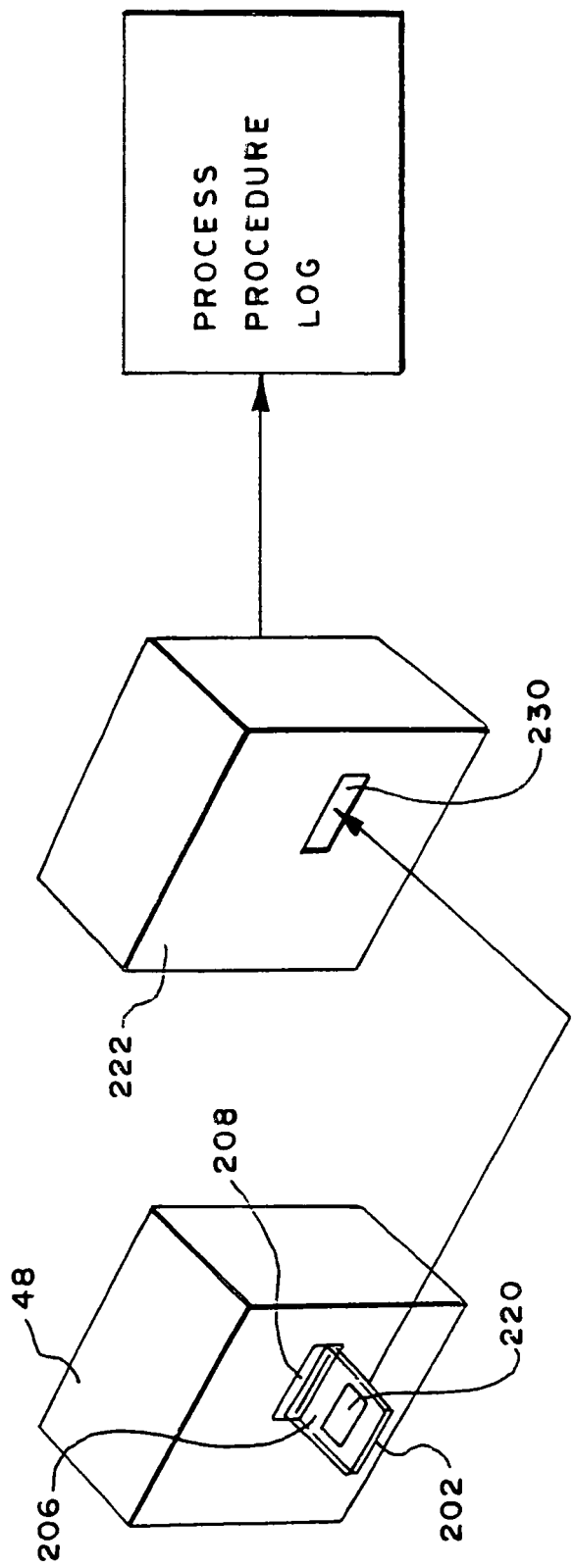

SYSTEMS AND METHODS FOR MONITORING AND CONTROLLING USE OF MEDICAL DEVICES

RELATED APPLICATION

This application is a divisional of U.S. patent application Ser. No. 10/974,454, filed Oct. 27, 2004 now U.S. Pat. No. 7,465,301, which is a divisional of U.S. patent application Ser. No. 09/974,750, filed Oct. 10, 2001 (now U.S. Pat. No. 6,827,713), which is a continuation of U.S. patent application Ser. No. 09/495,390, filed Jan. 30, 2000, and entitled "Systems and Methods for Monitoring and Controlling Use of Medical Devices," now abandoned.

FIELD OF THE INVENTION

The invention is directed to systems and methods for monitoring and controlling use of medical devices.

BACKGROUND OF THE INVENTION

Use of medical devices intended to treat or diagnose conditions of the body can sometimes generate stress on the material or materials from which the devices are made. The material stress can alter the physical characteristics of the devices., making future performance of the devices unpredictable.

In addition, exposure to blood and tissue during use can entrap biological components on or within many medical devices. Despite cleaning and subsequent sterilization, the presence of entrapped biological components can lead to unacceptable pyrogenic reactions.

The effects of material stress and damage caused during a single use of a medical device, coupled with the possibility of pyrogen reactions even after resterilization, reasonably justify imposing a single use restriction upon many medical devices.

SUMMARY OF THE INVENTION

The invention provides systems and methods for monitoring and controlling use of medical devices.

One aspect of the invention provides a kit containing a device for treating a tissue region. The kit also includes, packaged with the device, a usage key card. The usage key card comprises a storage medium, which is formatted to contain an identification code unique to the usage key card. The usage key card is adapted to be read by a remote reader, to download the identification code for processing by a controller for the device. Preestablished prior use criteria govern the processing of the identification code by the controller. Meeting the criteria permits operation of the device, conversely, not meeting the criteria disables use of the device.

In one embodiment, the storage medium is also formatted to retain data generated by the controller during permitted operation of the device. The data, e.g., pertains to operating conditions of the device, creating a procedure log. In this arrangement, the usage key card is adapted to be read by a reader, to download the procedure log for further processing by a separate data processing device.

Another aspect of the invention provides systems and methods for processing the identification code by the controller. The systems and methods cause the controller to create a table in memory in which unlike identification codes are registered as they are downloaded by the reader. The systems and methods enable operation of the device when a new identification code is registered in the table.

According to this aspect of the invention, the systems and methods cause the controller to compare a given identification code downloaded by the reader to all identification codes registered in the table. The systems and methods cause the controller to register the given identification code in the table when the given identification code does not match any identification code in the table. In this instance, operation of the device is permitted. Conversely, the systems and methods cause the controller not to register the given identification code when the given identification code matches an identification code already in the table. In this instance, operation of the device is not permitted.

In an embodiment that pertains to both aspects of the invention, the device operates to apply radio frequency energy to the tissue region.

Features and advantages of the inventions are set forth in the following Description and Drawings, as well as in the appended Claims.

BRIEF DESCRIPTION OF THE DRAWINGS

FIG. 9 is a schematic view of another processing device that reads information from the usage key card for further processing.

The invention may be embodied in several forms without departing from its spirit or essential characteristics. The scope of the invention is defined in the appended claims, rather than in the specific description preceding them. All embodiments that fall within the meaning and range of equivalency of the claims are therefore intended to be embraced by the claims.

DETAILED DESCRIPTION OF THE PREFERRED EMBODIMENTS

Figure 1:
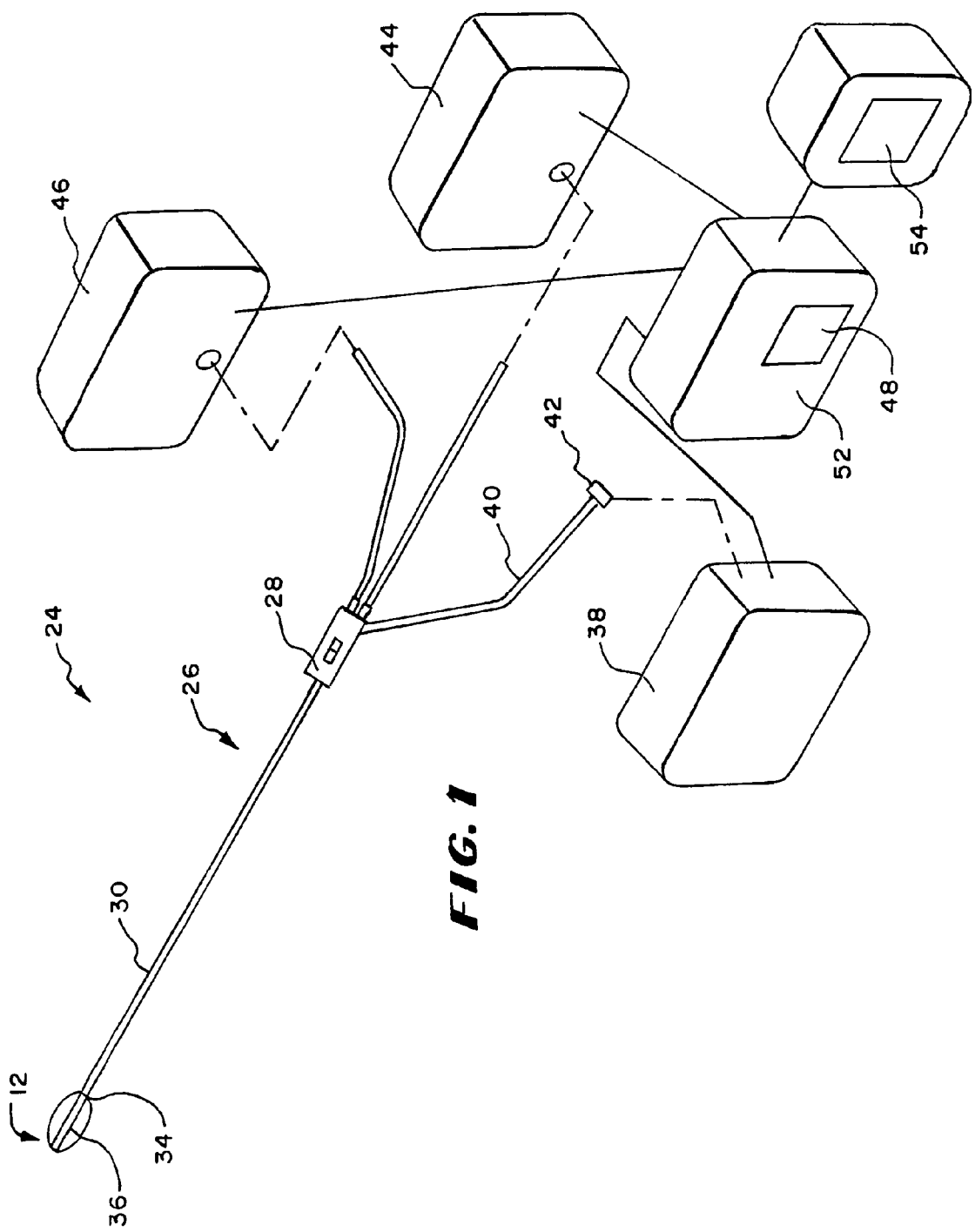
FIG. 1 is a diagrammatic view of a system for treating body sphincters and adjoining tissue regions, which embodies features of the invention.

FIG. 1 shows one embodiment of a system 10, which monitors and controls the use of an operative element 12. The system 10 is well adapted for association with single use, catheter-based devices. Therefore, in the illustrated embodiment, the operative element 12 is part of a catheter-based treatment device 26. It should be appreciated, however, that the system 10 is also adaptable for use with devices and methods that are not necessarily catheter-based.

A. The Treatment Device

In the illustrated embodiment, the device 26 includes a handle 28 made, e.g., from molded plastic. The handle 28 is sized to be conveniently held by a physician, to introduce the catheter tube 30 into the targeted tissue region.

The handle 28 carries a flexible catheter tube 30. The catheter tube 30 can be constructed, for example, using standard flexible, medical grade plastic materials. The catheter tube 30 has a distal end 34, which carries the operative element 12.

The operative element 12 can support, for example, a device for imaging body tissue, such as an endoscope, or an ultrasound transducer. The operative element 12 can also support a device to deliver a drug or therapeutic material to body tissue. The operative element 12 can also support a device for sensing a physiological characteristic in tissue, such as electrical activity, or for transmitting energy to stimulate or form lesions in tissue.

In the illustrated embodiment, the device 26, in use, is intended to treat dysfunction of sphincters and adjoining tissue regions in the upper gastrointestinal tract, e.g., in the lower esophageal sphincter and adjacent cardia of the stomach, as well as in the lower gastrointestinal tract, e.g., in the intestines, rectum and anal canal. Still, it should be appreciated that the system 10 can be used in association with other devices and methods used to treat other dysfunctions elsewhere in the body, which are not necessarily sphincter-related. For example, the various aspects of the invention have application in procedures requiring ablation of tissue throughout the body, or treatment of hemorrhoids, or restoring compliance to or otherwise tightening interior tissue or muscle regions.

In the illustrated embodiment, one function that the operative element 12 is to perform is to apply energy in a selective fashion to a targeted body region, which, for the purpose of illustration, can be the lower esophageal sphincter, or cardia, or both. The applied energy creates one or more lesions, or a prescribed pattern of lesions, below the mucosal surface of the esophagus or cardia. The subsurface lesions are formed in a manner that preserves and protects the mucosal surface against thermal damage.

It has been discovered that natural healing of the-subsurface lesions leads to a physical tightening of the sphincter and/or adjoining cardia. The subsurface lesions can also result in the interruption of aberrant electrical pathways that may cause spontaneous sphincter relaxation. In any event, the treatment can restore normal closure function to the sphincter.

Figure 2:
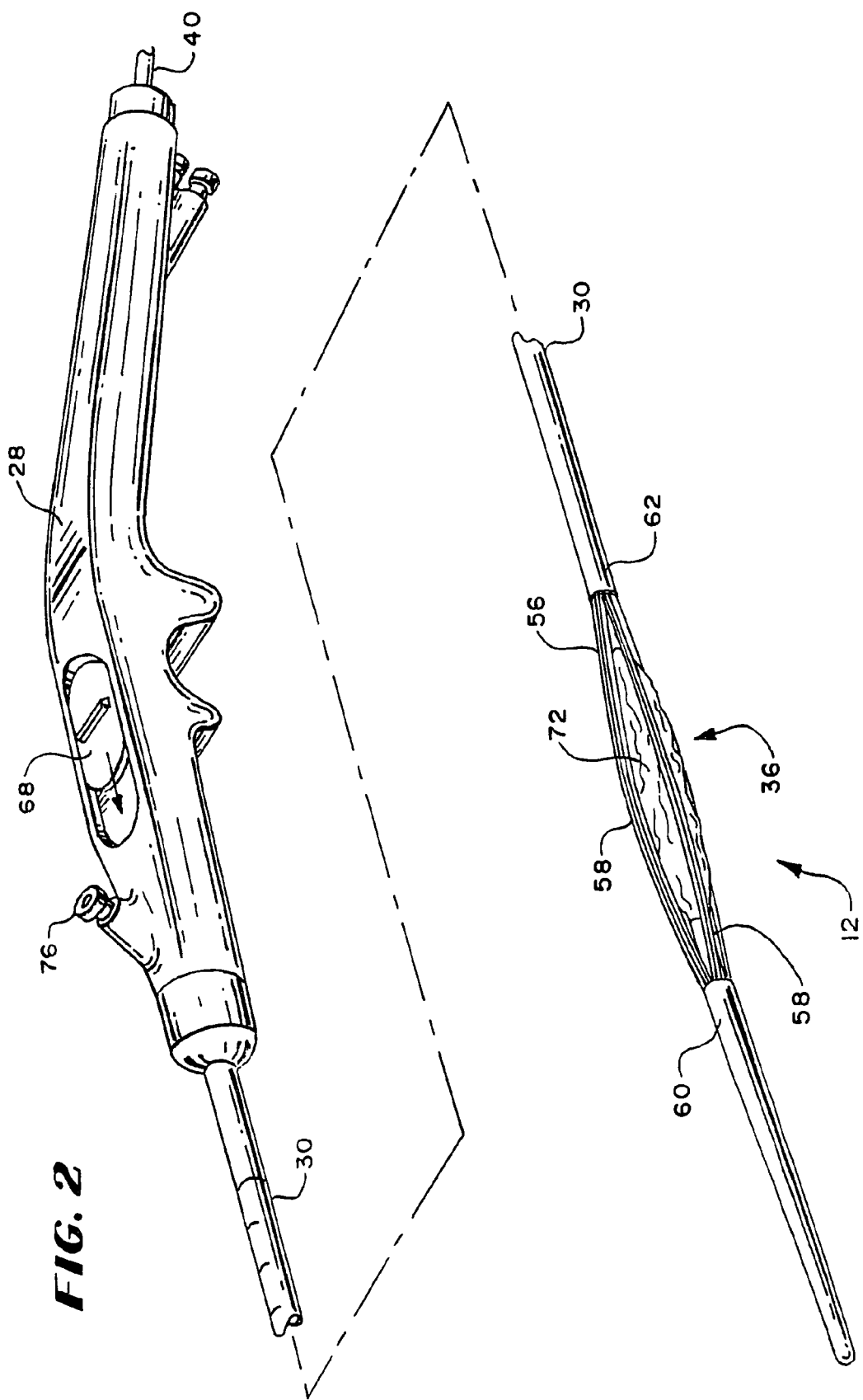
FIG. 2 is a perspective view, with portions broken away, of a device usable in association with the system shown in FIG. 1 having an operative element for contacting tissue shown in a collapsed condition.
Figure 3:
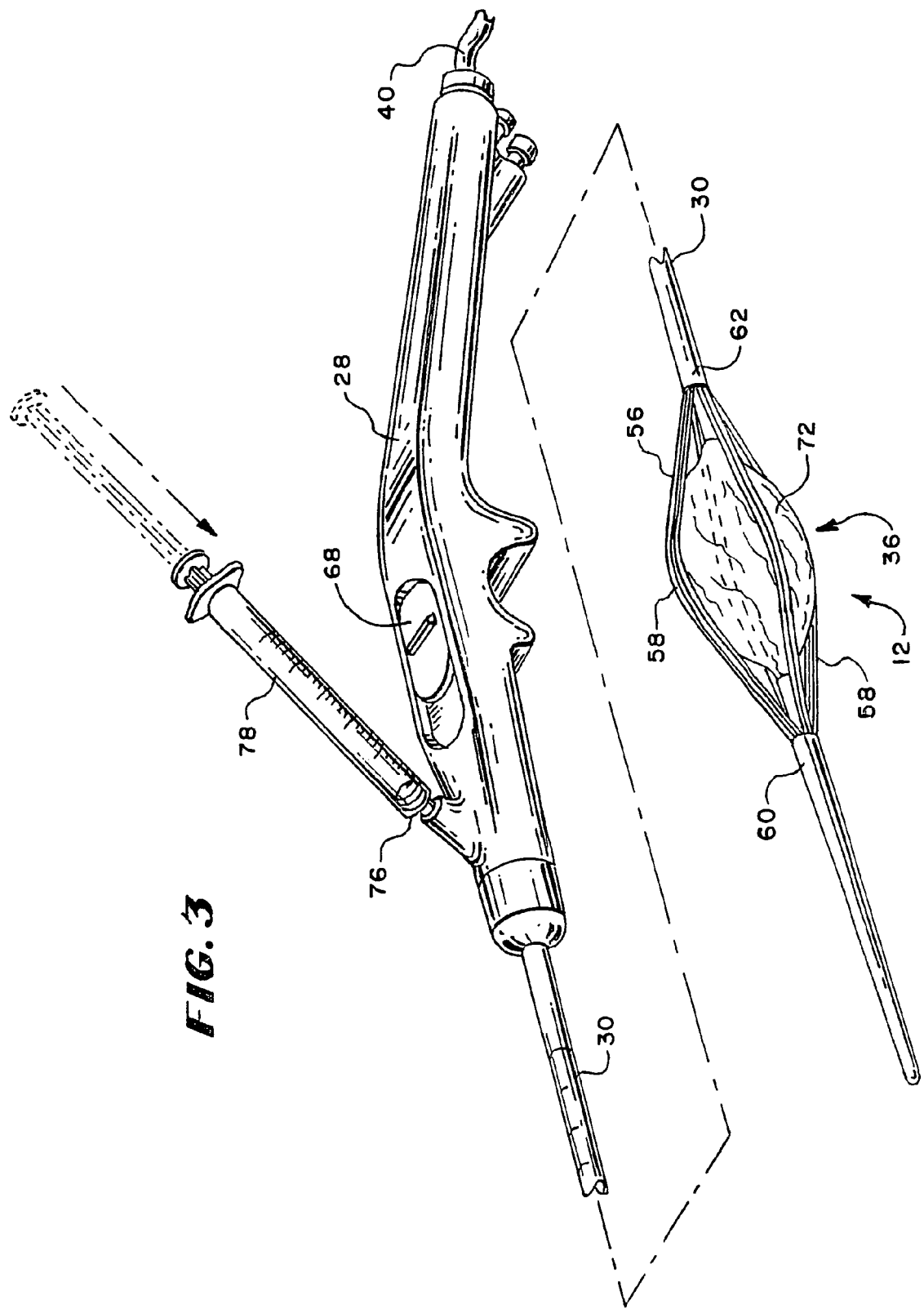
FIG. 3 is a perspective view, with portions broken away, of the device shown in FIG. 2, with the operative element shown in an expanded condition.
Figure 4:
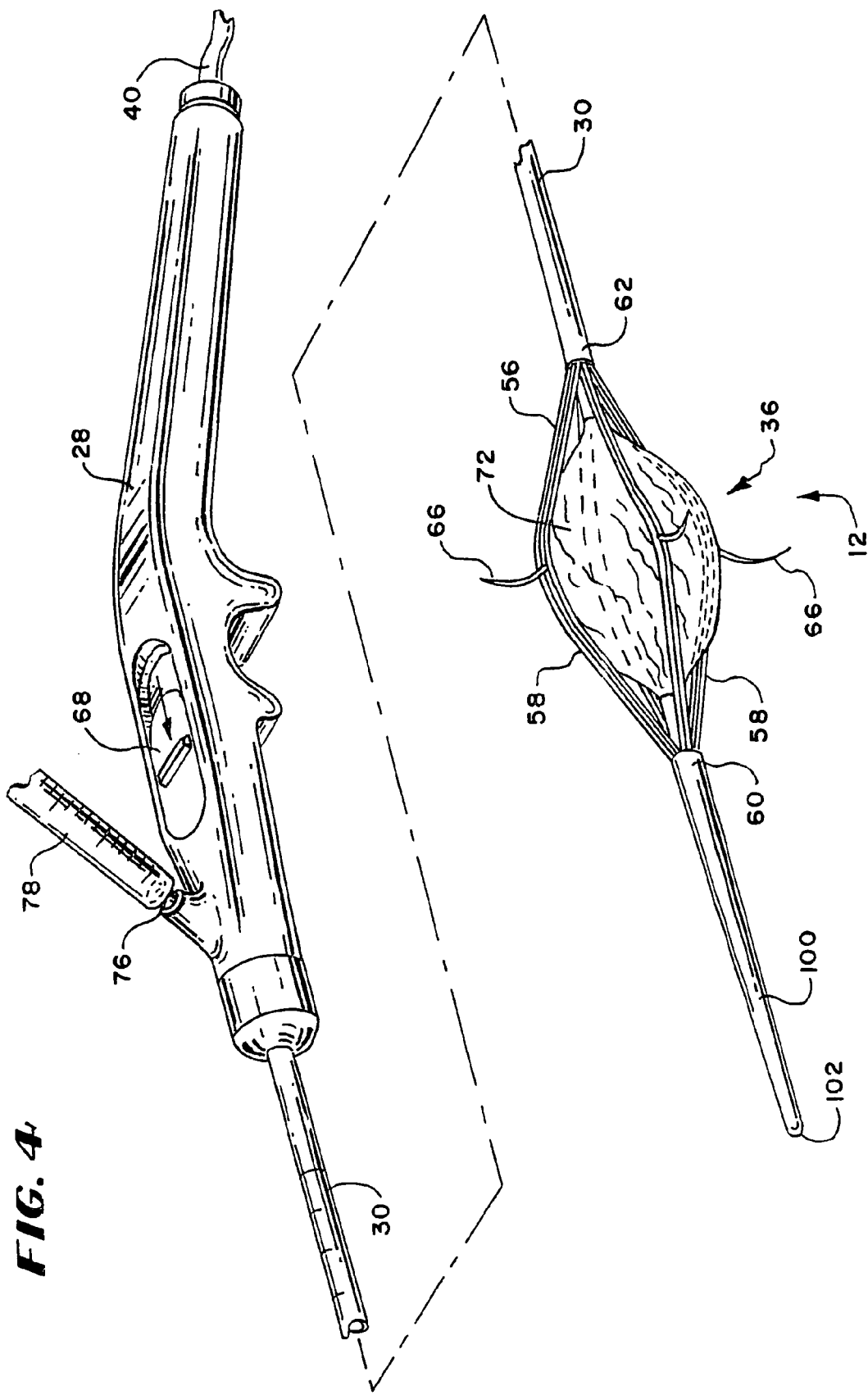
FIG. 4 is a perspective view, with portions broken away, of the device shown in FIG. 2, with the operative element shown in an expanded condition and the electrodes extended for use.

The structure of the operative element 12 to achieve this result can vary. A representative embodiment is shown in FIGS. 2 to 4, in which the operative element 12 comprises a three-dimensional basket 56. The basket 56 includes one or more spines 58, and typically includes from four to eight spines 58, which are assembled together by a distal hub 60 and a proximal base 62.

In the illustrated embodiment, an expandable structure 72 comprising a balloon is located within the basket 56. The balloon structure 72 can be made, e.g., from a Polyethylene Terephthalate (PET) material, or a polyamide (non-compliant) material, or a radiation cross-linked polyethylene (semi-compliant) material, or a latex material, or a silicone material, or a C-Flex (highly compliant) material.

The balloon structure 72 presents a normally, generally collapsed condition, as FIG. 2 shows. In this condition, the basket 56 is also normally collapsed about the balloon structure 72, presenting a low profile for deployment into the esophagus 10.

The catheter tube 30 includes an interior lumen, which communicates with the interior of the balloon structure 72. A fitting 76 (e.g., a syringe-activated check valve) is carried by the handle 28. The fitting 76 communicates with the lumen. The fitting 76 couples the lumen to a syringe 78 (see FIG. 3). The syringe 78 injects fluid under pressure through the lumen into the balloon structure 72, causing its expansion.

Expansion of the balloon structure 72 urges the basket 56 to open and expand (see FIG. 3). The force exerted by the balloon structure 72, when expanded, is sufficient to exert an opening force upon the tissue surrounding the basket 56.

Each spine 58 carries an electrode 66 (see FIG. 4). In the illustrated embodiment, each electrode 66 is carried within the tubular spine 58 for sliding movement. Each electrode 66 slides from a retracted position, withdrawn in the spine 58 (shown in FIG. 3) and an extended position, extending outward from the spine 58 (see FIG. 4) through a hole in the spine 58. A push-pull lever 68 on the handle 28 is coupled by one or more interior wires to the sliding electrodes 66. The lever 68 controls movement electrodes between the retracted position (by pulling rearward on the lever 68) and the extended position (by pushing forward on the lever 68). The electrodes 66 have sufficient distal sharpness and strength, when extended, to penetrate a desired depth into tissue the smooth muscle of the esophageal or cardia 20 wall. The desired depth can range from about 4 mm to about 5 mm.

In this arrangement (see FIG. 1), the system 10 includes a generator 38 to supply the treatment energy to the electrodes 66. In the illustrated embodiment, the generator 38 supplies radio frequency energy, e.g., having a frequency in the range of about 400 kHz to about 10 mHz. Of course, other forms of energy can be applied, e.g., coherent or incoherent light; heated or cooled fluid; resistive heating; microwave; ultrasound; a tissue ablation fluid; or cryogenic fluid.

A cable 40 extending from the proximal end of the handle 28 terminates with an electrical connector 42. The cable 40 is electrically coupled to the operative element 12, e.g., by wires that extend through the interior of the handle 28 and catheter tube 30. The connector 42 plugs into the generator 38, to convey the generated energy to the operative element 12.

The electrodes 66 are formed of material that conducts radio frequency energy, e.g., nickel titanium, stainless steel, e.g., 304 stainless steel, or a combination of nickel titanium and stainless steel.

Figure 5:
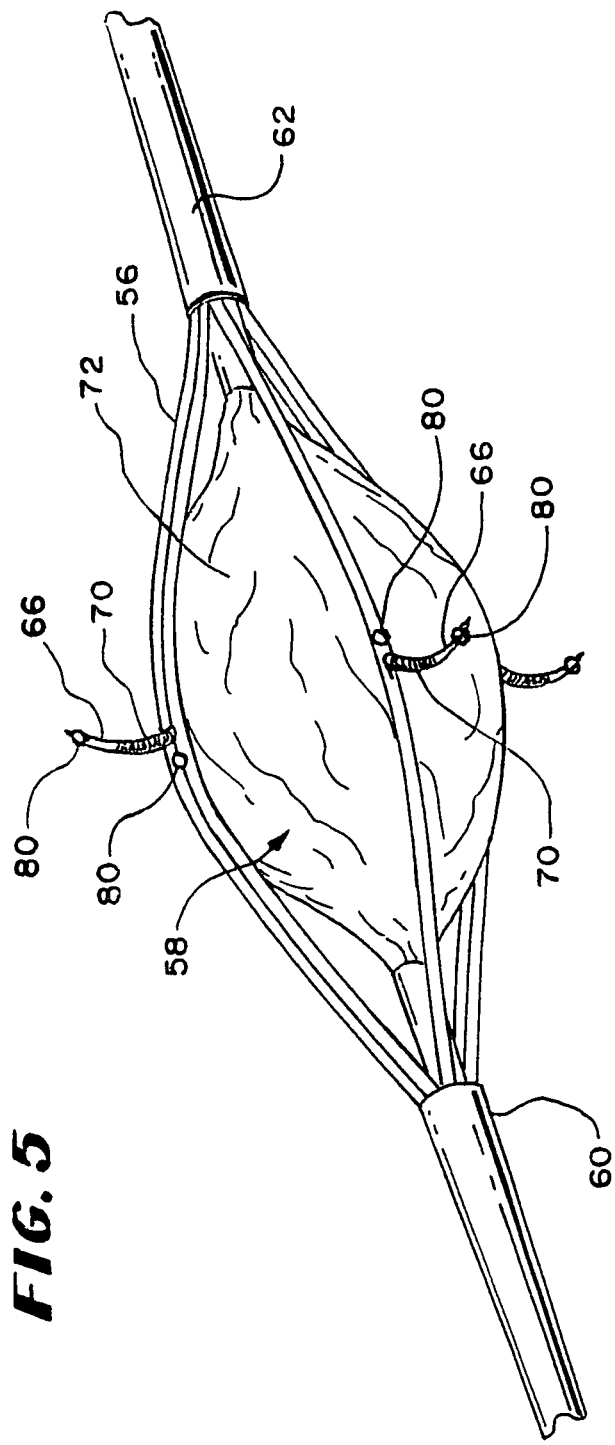
FIG. 5 is an enlarged view of the operative element shown in FIG. 4, with the electrodes extended for use.

In the illustrated embodiment (see FIG. 5), an electrical insulating material 70 is coated about the proximal end of each electrode 66. When the distal end of the electrode 66 penetrating the smooth muscle of the esophageal sphincter 18 or cardia 20 transmits radio frequency energy, the material 70 insulates the mucosal surface of the esophagus 10 or cardia 20 from direct exposure to the radio frequency energy. Thermal damage to the mucosal surface is thereby avoided. The mucosal surface can also be actively cooled during application of radio frequency energy, to further protect the mucosal surface from thermal damage.

In the illustrated embodiment (see FIG. 5) at least one temperature sensor 80 is associated with each electrode. One temperature sensor 80 senses temperature conditions near the exposed distal end of the electrode 66, a second temperature sensor 80 is located on the corresponding spine 58, which rests against the muscosal surface when the balloon structure 72 is inflated.

The system 10 (see FIG. 1) can also include certain auxiliary processing equipment, e.g., an external fluid delivery apparatus 44 for supplying cooling liquid to the targeted tissue, e.g., through holes in the spines, and an external aspirating apparatus 46 for conveying liquid from the targeted tissue site, e.g., through other holes in the spine or elsewhere on the basket 56.

The system 10 also includes a controller 52. The controller 52, which preferably includes a central processing unit (CPU), is linked to the generator 38, the fluid delivery apparatus 44, and the aspirating apparatus 46. Alternatively, the aspirating apparatus 46 can comprise a conventional vacuum source typically present in a physician's suite, which operates continuously, independent of the controller 52. The controller 52 governs the delivery of processing fluid and, if desired, the removal of aspirated material.

The controller 52 also governs the power levels, cycles, and duration that the radio frequency energy is distributed to the electrodes 66, to achieve and maintain power levels appropriate to achieve the desired treatment objectives. The controller 52 can condition the electrodes 66 to operate in a monopolar mode. In this mode, each electrode 66 serves as a transmitter of energy, and an indifferent patch electrode (not shown) serves as a common return for all electrodes 66. Alternatively, the controller 52 can condition the electrodes 66 to operate in a bipolar mode. In this mode, one of the electrodes comprises the transmitter and an other electrode comprises the return for the transmitted energy. The bipolar electrode pairs can electrodes 66 on adjacent spines, or electrodes 66 spaced more widely apart on different spines.

The controller 52 includes an input/output (I/O) device 54. The I/O device 54 allows the physician to input control and processing variables, to enable the controller to generate appropriate command signals. The I/O device 54 also receives real time processing feedback information from the temperature sensors 80, for processing by the controller 52, e.g., to govern the application of energy and the delivery of processing fluid. The I/O device 54 also includes a graphical user interface (GUI), to graphically present processing information to the physician for viewing or analysis.

B. Monitoring and Control of Reuse

The handle 28 and the catheter tube 30 form an integrated construction intended for a single use and subsequent disposal as a unit. Alternatively, the handle 28 can comprise a nondisposable component intended for multiple uses. In this arrangement, the catheter tube 30, and components carried at the end of the catheter tube 30 comprise a disposable assembly, which the physician releasably connects to the handle 28 at time of use and disconnects and discards after use. The catheter tube 30 can, for example, include a male plug connector that couples to a female plug receptacle on the handle 28.

To protect patients from the potential adverse consequences occasioned by multiple use, which include disease transmission, or material stress and instability, or decreased or unpredictable performance, the controller 54 includes a module 48 that controls use of the device 26.

In the illustrated embodiment (see FIG. 6), the device 26 is supplied as part of a kit 200 that includes, together with the device 26, a usage key card 202. The kit 200 packages the device 26 and usage key card 202 as a unitary, single use item in a sterile fashion within peripherally sealed sheets of plastic film material that are torn or peeled away at the instance of use.

The presence of the device 26 and user key card 200 packaged together in the kit 200 verifies to the physician or user that device 26 is sterile and has not be subjected to prior use. The physician or user is thereby assured that the device 26 meets established performance and sterility specifications. No unused device 26 is supplied in the kit 200 without a usage key card 202, and vice versa.

The usage key card 202 incorporates a storage medium 204 that is readable by the module 48. The storage medium 204 contains information that enables at least two use control and monitoring functions.

The first use control and monitoring function of the usage key card 202 occurs prior to use of the device 26 in association with the generator 38. To enable use of the generator 38 in association with the device 26, the physician must first present the usage key card 202 for reading by the module 48. To enable use of the device 26, the controller 54 must then find that the usage key card 202 meets the criteria necessary for its registration by the controller 54. The criteria are designed to indicate the absence of a prior use, either in absolute terms or in terms of a period of use outside a predetermined time period. If the criteria are not met, the controller 54 will not register the usage key card 202, and the controller 54 will also not enable use of the generator 38 in association with the device 26. Further details of the registration function of the controller 54 will be described later.

The second use control and monitoring function of the usage key card 202 occurs if the criteria are met and registration of the usage key card 202 occurs. During permitted use of the device 26 in association with the generator 38, the storage medium 204 of the usage key card 202 remains in the module 48 and receives, via the module 48, data generated by the controller 54 recording operating parameters and performance of the device 26. The storage medium 204 of the usage key card 202 retains and organizes the data for further off-line storage and processing. Further details of the data retention function will be described later.

The usage key card 202 can be variously configured. In the illustrated embodiment (see FIG. 7), the usage key card 202 comprises a computer-readable storage medium 204 housed within a conventional 3.5 inch floppy disk 206. In this arrangement, the module 48 comprises a conventional floppy disk drive 208 (see FIG. 8) capable of reading data from and downloading data to the storage medium 204 of the disk 206.

Alternatively, the usage key card 202 can take the form of a PC card, flash memory device, or magnetic card. In these alternative embodiments, the module 48 comprises a data reading and writing device compatible with the storage medium of the card 202.

Figure 7:
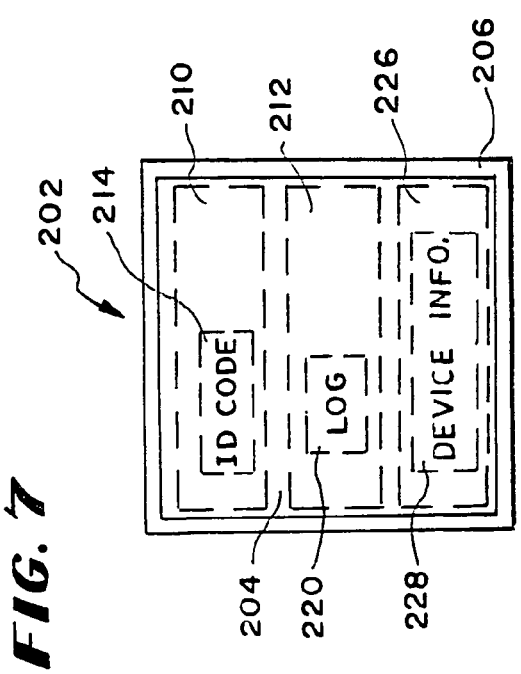
FIG. 7 is an enlarged, mainly schematic view of the usage key card shown in FIG. 6, embodied as a floppy disk, and also showing the pre-formatted files it contains.

As FIG. 7 shows, the storage medium 204 of the usage key card 202 contains at least two pre-formatted files 210 and 212. The first file 210 contains a unique identification code 214 capable of being read by the module 48 and registered by the controller 54. The second file 212 is formatted to receive and retain operational and performance data generated by the controller 54 to create from it a procedure log 220.

The identification code 214 contained in the first file 210 is created to be unique to the particular usage key card 202. That is, each usage key card 202 contains its own unique identification code 214. No two usage key cards share the same identification code 214. The unique identification code 214 can comprise, e.g., a serial number uniquely assigned to the particular device 26 found in the kit 200, or any other unique code that is not repeated for any other usage key card 202. The code 214 itself can comprise letters, numbers, or combinations thereof.

Figure 8:
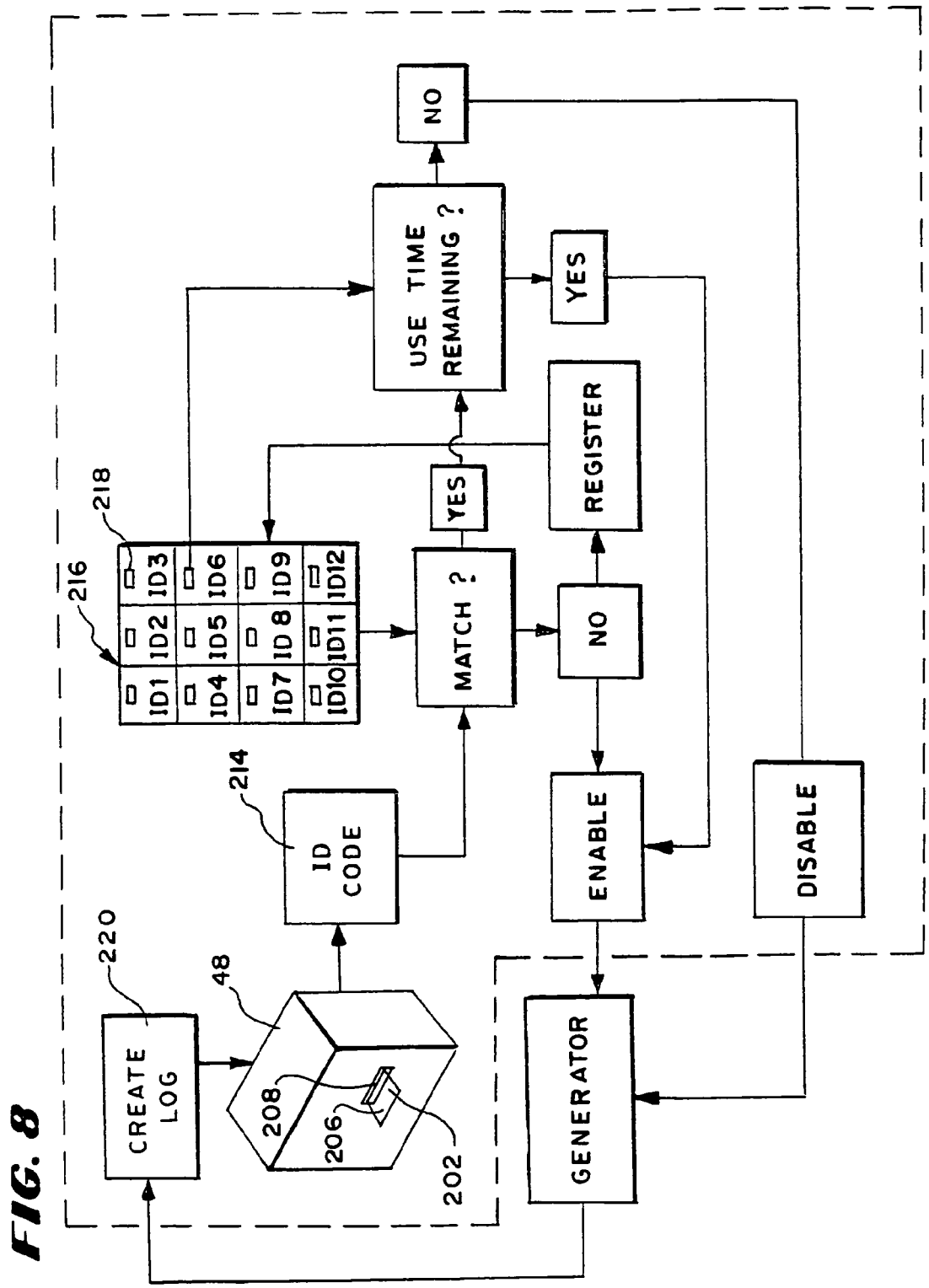
FIG. 8 is a schematic view of a controller, which the system shown in FIG. 1 incorporates, showing the pre-programmed rules by which information contained on the usage key card shown in FIGS. 6 and 7 is read and processed.

As FIG. 8 shows, the module 48 reads the identification code 214 off the usage key card 202 for input to the controller 54. This identification code will be called the "instant identification code."

Following pre-programmed rules, the controller 54 constructs and maintains in non-volatile memory a use table 216. The use table 216 contains all prior identification codes that meet the criteria to be registered by the controller 54. These identification codes will be called the "registered identification codes." Following pre-programmed rules, the controller 54 compares the instant identification code 214 to all registered identification codes contained in the table 216. In the absence of a match between the instant identification code and any registered identification code, the controller 54 updates the table, i.e., the controller registers the instant identification code by adding it to the table 216. Upon registering the usage key card 202, the controller 54 also enables use of generator 38 in association with the device.

The presence of a match between the instant identification code and any registered identification code indicates the usage key card 202 has been previously read by the module 48, which reflects a prior use of the device 26 or another device not packaged with the card 202. In this circumstance, the controller 54 does not add the duplicative identification code to the table 216 and does not enable use of the generator 38 in association with any device 26. Preferably, the controller 54 outputs to the GUI notice of prior use.

In an alternative arrangement, the controller 54 maintains for each registered identification code in the table 216 a time record 218. The time record 218 contains a value reflecting the period of time during which energy was applied by the generator 38 during the previous permitted use. In this embodiment, when a match occurs between the instant identification code and a registered identification code, the controller 54 ascertains whether the time period of previous use contained in the record 218 is less than a prescribed maximum time period, e.g., 45 minutes. If so, the controller 54 enables a subsequent operation of the generator 38 in association with the device 26, but only for the time period remaining. The controller 54 updates the time record 218 as further use occurs. The controller 54 preferably outputs to the GUI the time period of permitted use remaining.

If the controller 54 ascertains that the time period of previous use equals or exceeds the prescribed maximum time period, the controller 54 does not enable use of the generator 38. Preferably, the controller 54 outputs to the GUI notice of prior use.

As FIG. 9 shows, the second file 212 contained on the storage medium 204 of the usage key card 202 is formatted to receive, via the module 48, data that is generated by the controller 54 during permitted use of the device 26 in association with the generator 38. The file 212 retains the data in a formatted array according to pre-programmed rules to create a procedure log 220.

The content of the formatted log 220 can vary. For example, the log 220 can document, by date of treatment and number of treatments, the coagulation level (i.e., the depth at which the electrodes are inserted), the time duration of energy application, the magnitude of energy delivered by each electrode, and the coolant flow rate. The procedure log 220 can also record at pre-established intervals (e.g., every 5 seconds) the temperatures of the electrodes and surrounding tissue, along other parameters e.g., sensed impedance and power delivered by each electrode. The procedure log 220 preferably records these values in a pre-formatted data base format, to enable import of the values as data base items for storage, processing1 and retrieval by an off-line data processing device 222 having a compatible data base processing application. The off-line data processing device 222 reads processing log data from the usage key card 202 (via a floppy disk drive 230 or otherwise compatible reading device).

The device 222 can process the data in various ways according to the rules of the data processing application. The device 222 can, e.g., create a print-formatted record of the procedure log 220 for printing in a hard copy version. The device 222 can also, e.g., process the procedure logs for multiple devices and patients, to create historical patient treatment records, patient reimbursement records, and the like for storage or retrieval. The device 222 thereby makes possible the establishment and maintenance of an archival patient data base by processing individual procedure logs.

Figure 6:
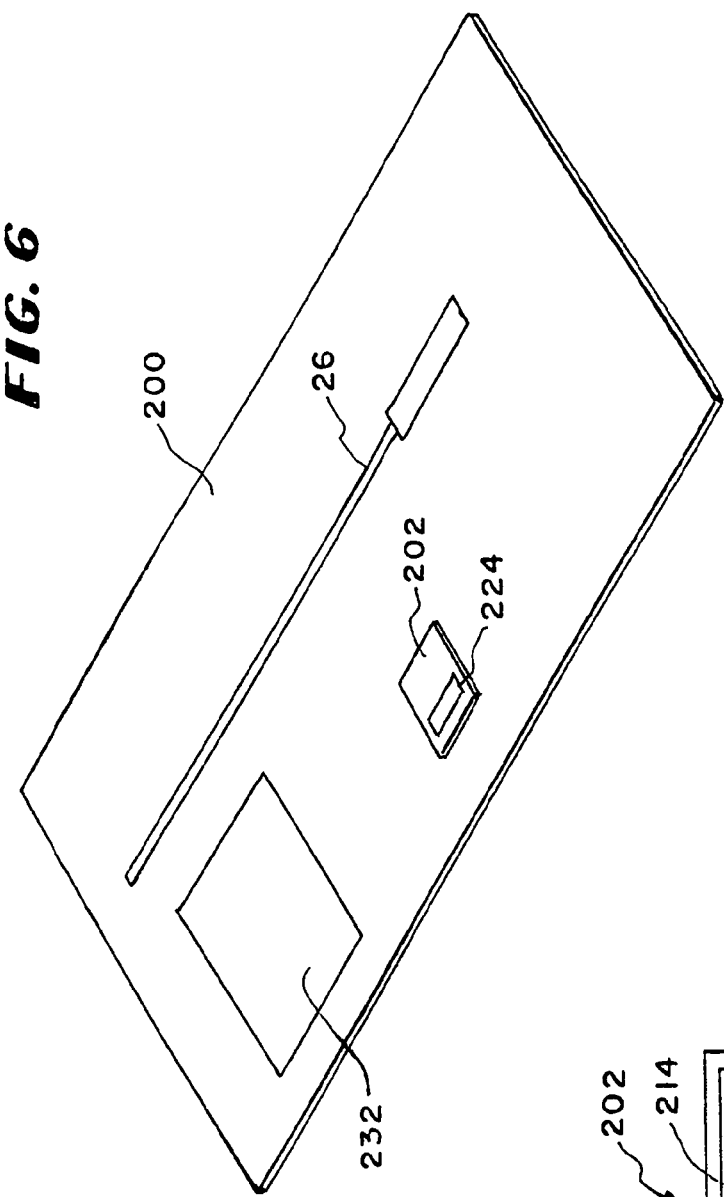
FIG. 6 is a perspective view of a kit containing a device, such as shown in FIGS. 2 to 5, and a usage key card.

As FIG. 6 shows, the kit 200 can also include a label 224 that is pre-applied or that can be applied by the physician to the usage key card 202. The label 224 receives manually transcribed, visually readable information pertaining to the usage key card 202, e.g., the name of the patient being treated by the device 26, the date of treatment, and the like. In this way, usage key cards 202 can itself be physically stored and indexed.

As FIG. 6 also shows, the kit 200 can also include instructions 232 for using the usage key card 202 in the fashion described. For example, the instructions 232 can instruct the physician as to the need for having the usage key card 202 read by the module 48, in order to enable use of the device 26 in association with the generator 38. The instructions 232 can also instruct the physician regarding the content of the procedure log and the subsequent off-line processing options that are available.

As FIG. 7 shows, the storage medium 204 of the usage key card 202 can also contain at least one additional formatted file 226 that provides device information 228, which characterizes the device 26 supplied in the kit 200. For example, the device information 228, when read by the module 48, can identify the type of device 26 in terms of its operational characteristics, the inclusion of temperature sensing, and reuse criteria (e.g., no reuse after a single use, or multiple uses permitted up a prescribed maximum number of uses, or multiple uses permitted up to a maximum time period of use, or multiple uses permitted up to a maximum application of RF energy). The file 226 can also condition the GUI to display the desired images and data formats, which change depending upon the treatment procedure using the device (e.g. treatment of GERD, fecal incontinence, or urinary incontinence). In one arrangement, the controller 54 can compare the device characteristics with the operational characteristics of the controller 54 and generator 38, and disable operation of the device 26 should the characteristics of the device 26 be incompatible with the characteristics of the controller 54 and/or generator 38.

Various features of the invention are set forth in the following claims.

We claim:

1. A system comprising
a device for treating a tissue region, and
a usage key card not connected to the device to be handled separate from the device comprising a storage medium formatted to contain an identification code uniquely assigned to the device, the identification code being unique to the usage key card, the usage key card being adapted to be read by a reader separate from the device, the storage medium being also formatted, when inserted into the reader, to retain data generated during operation of the device pertaining to operation of the device, the reader downloading the identification code to a controller to update a use table and register the identification code if not previously registered upon being downloaded to enable use of the device upon being registered.

2. A system according to claim 1 wherein the usage key card comprises a floppy disk.

3. A system according to claim 1 wherein the usage key card comprises a PC card.

4. A system according to claim 1 wherein the usage key card comprises a magnetic card.

5. A system according to claim 1 wherein the usage key card comprises flash memory.

6. A system according to claim 1 wherein the device applies radio frequency energy to the tissue region.

7. A system according to claim 1 wherein when the usage key card is inserted into the reader and the reader downloads the identification code to the controller the use table is not updated if the identification code is previously registered.

8. A system according to claim 1 wherein the storage medium contains at least first and second pre-formatted files, the first file containing the identification code and the second file containing operational and performance data.

9. A system according to claim 8 wherein the second file receives data generated by the controller during permitted use of the device.

10. A system according to claim 9 wherein the second file retains the data in a formatted array to create a procedure log.

11. A system according to claim 10 wherein the procedure log documents by date of treatment a magnitude of energy delivered by the device.

12. A system according to claim 10 wherein the procedure log documents by date of treatment a time duration of energy application.

13. A system comprising
a device for treating a tissue region; and
a storage medium associated with the device, the storage medium formatted to contain an identification code uniquely assigned to the device, the storage medium adapted to be read by a reader separate from the device for downloading the identification code to a controller to enable the controller to add to its registry the downloaded identification code if not already in its registry upon being downloaded to enable use of the device upon being added to its registry and to not add the identification code to its registry if already in its registry.

14. A system according to claim 13 wherein the storage medium contains at least first and second pre-formatted files, the first file containing the identification code and the second file containing operational and performance data.

15. A system according to claim 14 wherein the second file receives data generated by the controller during permitted use of the device.

16. A system according to claim 15 wherein the second file retains the data in a formatted array to create a procedure log.

17. A system according to claim 16 wherein the procedure log documents by date of treatment a magnitude of energy delivered by the device.

18. A system according to claim 16 wherein the procedure log documents by date of treatment a time duration of energy application.

\* \* \* \* \*